(12) United States Patent
Taneda

(10) Patent No.: US 10,203,309 B2
(45) Date of Patent: Feb. 12, 2019

(54) CHROMATOGRAM DISPLAY METHOD, CHROMATOGRAM DISPLAY DEVICE, AND CHROMATOGRAPH COMPRISING SAID DEVICE

(71) Applicant: SHIMADZU CORPORATION, Kyoto-shi, Kyoto (JP)

(72) Inventor: Katsuyuki Taneda, Kyoto (JP)

(73) Assignee: SHIMADZU CORPORATION, Kyoto-shi, Kyoto (JP)

( * ) Notice: Subject to any disclaimer, the term of this patent is extended or adjusted under 35 U.S.C. 154(b) by 93 days.

(21) Appl. No.: 14/499,646

(22) Filed: Sep. 29, 2014

(65) Prior Publication Data

US 2015/0168360 A1 Jun. 18, 2015

(30) Foreign Application Priority Data

Dec. 17, 2013 (JP) .................................. 2013-259932

(51) Int. Cl.
*G01N 30/00* (2006.01)
*G01N 30/86* (2006.01)
*G01N 30/78* (2006.01)
*G01N 30/68* (2006.01)

(52) U.S. Cl.
CPC ......... *G01N 30/8665* (2013.01); *G01N 30/78* (2013.01); *G01N 30/8672* (2013.01); *G01N 30/68* (2013.01)

(58) Field of Classification Search
CPC ............... G01N 30/68; G01N 30/7206; G01N 30/7213; G01N 30/78; G01N 30/8668; G01N 30/8672; G01N 30/8651
See application file for complete search history.

(56) References Cited

U.S. PATENT DOCUMENTS

| 8,134,121 B2* | 3/2012 | Miyagawa | G01N 30/7206 250/282 |
| 8,378,293 B1* | 2/2013 | Quimby | H01J 49/0027 134/2 |
| 2008/0296487 A1* | 12/2008 | Lubkowitz | G01N 30/78 250/283 |
| 2015/0107331 A1* | 4/2015 | Wang | G01N 30/72 73/23.37 |

FOREIGN PATENT DOCUMENTS

JP 60-239669 A 11/1985

* cited by examiner

*Primary Examiner* — Blake A Tankersley
(74) *Attorney, Agent, or Firm* — Sughrue Mion, PLLC

(57) ABSTRACT

Chromatographs of a measurement target sample measured in FID and MS are displayed on display unit in a time range defined with reference to the retention index of the target component computed based on the standard retention time and calibration retention time for the target component in FID. The retention index is not readily influenced by difference in column length, thus making it possible to display the peaks of the target component measured with FID and MS in a corresponding time range by displaying the chromatograms on display unit in a time range defined with reference that retention index. Therefore, even in cases where the retention times of the target component in FID and MS are different, measurement results for an identical target component from FID and MS can be easily compared.

19 Claims, 6 Drawing Sheets

CHROMATOGRAM DISPLAY METHOD, CHROMATOGRAM DISPLAY DEVICE, AND CHROMATOGRAPH COMPRISING SAID DEVICE

TECHNICAL FIELD

The present invention relates to a chromatogram display method and chromatogram display device for displaying, on a display unit, chromatograms of a measurement target sample containing an identical target component measured using a first detector and a second detector, and to a chromatograph comprising said device.

BACKGROUND ART

In a chromatograph, a sample (measurement target sample) is separated into components in the process of passing through a column, and the separated components are detected with a detector. The measurement results obtained with such a chromatograph are displayed on a display unit as a chromatogram with time as the horizontal axis and detection signal intensity as the vertical axis. Peaks of the components contained in the sample appear on the chromatogram.

For example, in cases where the sample is a food product or biological sample, since there are relatively many interference components contained in the sample, numerous peaks will appear on the chromatogram. Thus, there are cases where it is difficult to accurately identify a target component contained in the sample based solely on the detection signal from one detector. In this connection, a method for identifying a target component by measuring a sample using multiple detectors and comparing the measurement results thereof is known (for example, see undermentioned Patent literature 1).

Examples of a detector include FID (Flame Ionization Detector), ECD (Electron Capture Detector), FPD (Flame Photometric Detector), as well as mass spectrometers and the like. An ECD can selectively measure chlorine agrochemicals and an FPD can selectively measure organophosphate agrochemicals, thus limiting the peaks which appear on the chromatogram obtained through measurement of a sample. In addition, if the sample is measured with a mass spectrometer, target components can be identified with good precision.

PRIOR ART LITERATURES

Patent Literatures (Patent literature 1) Japanese Unexamined Patent Application Publication S60-239669

SUMMARY OF THE INVENTION

Problem to be Solved by the Invention

When a sample is measured using multiple detectors as described above, even with an identical target component, the retention time for the respective measurement results will not be identical. This may be due to differences in measurement conditions, such as column type, but even assuming that there are no such differences, since it is difficult to make the column length identical, it is difficult to make the retention times completely identical. Thus, there is the problem that the measurement results for an identical target component from the various detectors cannot be easily compared.

Furthermore, in order to compare the measurement results for an identical target component from different detectors, it is necessary to determine the standard retention time of the target component in each detector in advance by measuring a standard sample containing the target component with each detector, and to identify the target component from the measurement results of each detector based on those standard retention times. Thus, there is the problem that comparing the measurement results for an identical target component from different detectors is time-consuming.

The present invention was made in light of the aforementioned circumstances, its object being to provide a chromatogram display method, chromatogram display device, and chromatograph comprising said device, which make it possible to easily compare the measurement results for an identical target component from different detectors. It is a further object of the present invention to provide a chromatogram display method, chromatogram display device, and chromatograph comprising said device, which make it possible to reduce the time required to compare the measurement results for an identical target component from different detectors.

Means for Solving the Problem

The chromatogram display method according to the present invention is a method for displaying, on a display unit, chromatograms of a measurement target sample containing an identical target component measured using a first detector and a second detector, said method comprising: a standard retention time determination step, a first calibration retention time determination step, a retention index computation step, a second calibration retention time determination step, a standard retention time computation step, and a display processing step.

In the standard retention time determination step, the standard retention time of the target component in the first detector is determined by measuring a standard sample containing the target component with the first detector. In the first calibration retention time determination step, the calibration retention time in the first detector is determined by measuring a calibration sample containing a calibration component with the first detector. In the retention index computation step, a retention index for the target component is computed based on the standard retention time and calibration retention time for the target component in the first detector. In the second calibration retention time determination step, the calibration retention time in the second detector is determined by measuring the calibration sample with the second detector. In the standard retention time computation step, the standard retention time of the target component in the second detector is computed based on the calibration retention time in the second detector and the retention index. In the display processing step, chromatograms of the measurement target sample measured with the first detector and the second detector are displayed on the display unit in a time range defined with reference to the retention index.

Based on this configuration, chromatograms of a measurement target sample measured in the first detector and second detector are displayed on the display unit in a time range defined with reference to the retention index of the target component computed based on the standard retention time and calibration retention time for the target component in the first detector. Since the retention index is not readily influenced by differences in column length, by displaying chromatograms in a time range defined with reference to that time index, it becomes possible to display the peaks of the target component, measured with the different detectors, in a corresponding time range. Therefore, even in cases where the retention times of the target component in the detectors differ, the measurement results for an identical target component from each detector can be easily compared.

Furthermore, the standard retention time of the target component in the second detector is computed on the basis of the calibration retention time in the second detector and the retention index of the target component computed based on the standard retention time and calibration retention time for the target component in the first detector. Consequently, there is no need to measure a standard sample containing the target component with the second detector in order to determine the standard retention time, and thus the time required to compare the measurement results for an identical target component from different detectors can be reduced.

In the display processing step, identification information for the target component identified by measuring the measurement target sample with the first detector may be displayed on the chromatogram of the measurement target sample measured with the second detector based on the retention index.

Based on this configuration, identification information for the target component identified by measuring the measurement target sample with the first detector can be displayed at a location corresponding to the retention time of the same target component on the chromatogram of the measurement target sample measured with the second detector. Therefore, the measurement results for the same target component from the different detectors can be compared even more easily.

In the display processing step, identification information for components other than the target component identified by measuring the measurement target sample with the second detector may be displayed on the chromatogram of the measurement target sample measured with the first detector based on the retention index.

Based on this configuration, identification information for components other than the target component identified by measuring the measurement target sample with the second detector can be displayed at a location corresponding to the retention of the same target component on the chromatogram of the measurement target sample measured with the first detector. Therefore, the measurement results not just for the target component but also for components other than the target component can be easily compared.

The chromatogram display device according to the present invention is a device for displaying, on a display unit, chromatograms of a measurement target sample containing an identical target component measured using a first detector and a second detector, the device comprising: a standard retention time determination unit, a first calibration retention time determination unit, a retention index computation unit, a second calibration retention time determination unit, a standard retention time computation unit, and a display processing unit.

The standard retention time determination unit determines the standard retention time of the target component in the first detector by measuring a standard sample containing the target component with the first detector. The first calibration retention time determination unit determines the calibration retention time in the first detector by measuring a calibration sample containing a calibration component with the first detector. The retention index computation unit computes a retention index for the target component based on the standard retention time and calibration retention time for the target component in the first detector. The second calibration retention time determination unit determines the calibration retention time in the second detector by measuring the calibration sample with the second detector. The standard retention time computation unit computes the standard retention time of the target component in the second detector based on the calibration retention time in the second detector and the retention index. The display processing unit displays chromatograms of the measurement target sample measured with the first detector and the second detector on the display unit in a time range defined with reference to the retention index.

The display processing unit may display identification information for the target component identified by measuring the measurement target sample with the first detector, on the chromatogram of the measurement target sample measured with the second detector, based on the retention index.

The display processing unit may display identification information for components other than the target component identified by measuring the measurement target sample with the second detector, on the chromatogram of the measurement target sample measured with the first detector, based on the retention index.

The chromatograph according to the present invention comprises: a first detection unit; a second detection unit; and a chromatogram display device.

Effect of the Invention

According to the present invention, even in cases where the retention times of the target component in different detectors are different, the measurement results for an identical target component from each detector can be easily compared. Furthermore, according to the present invention, since there is no need to determine the standard retention time by measuring a standard sample containing the target component with the second detector, the time required to compare the measurement results for an identical target component from each detector can be reduced.

DETAILED DESCRIPTION OF THE EXEMPLARY EMBODIMENTS

Figure 1:
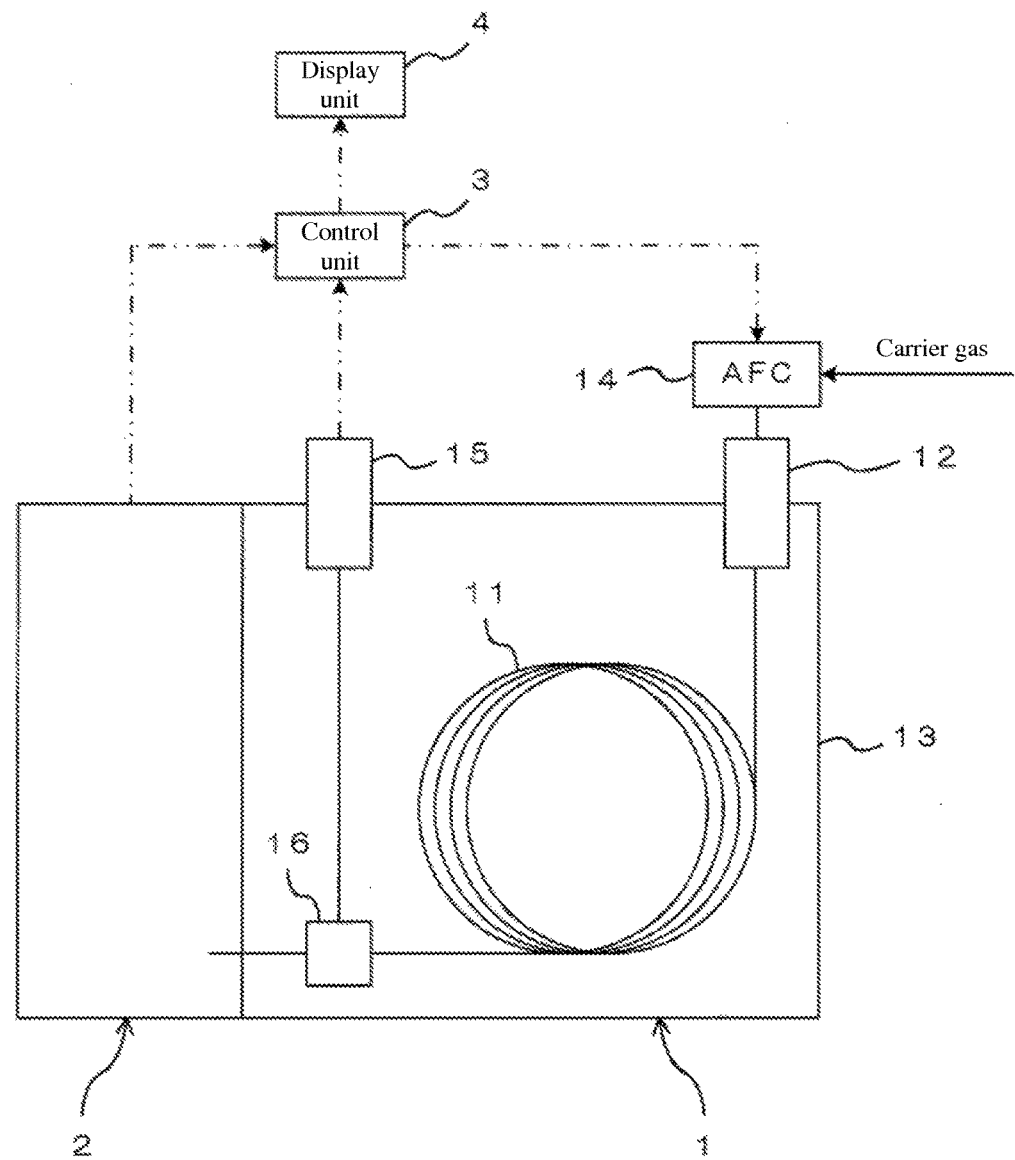
FIG. 1 is a simplified diagram illustrating an example of the configuration of a chromatograph according to an embodiment of the present invention.

FIG. 1 is a simplified diagram illustrating an example of the configuration of a chromatograph according to an embodiment of the present invention. This chromatograph is for example a gas chromatograph/mass spectrometer (GC/MS), comprising a gas chromatograph section (GC 1) and a mass spectrometry section (MS 2).

GC 1 comprises, for example, column 11, sample gasification chamber 12, column oven 13, AFC (Advanced Flow Controller) 14, FID (Flame Ionization Detector) 15 and splitter unit 16. Column 11 consists, for example, of a capillary column, the top end of which is connected to sample gasification chamber 12.

Sample and carrier gas are supplied to the sample gasification chamber 12, and sample components gasified in sample gasification chamber 12 are introduced along with carrier gas into the column 11. In GC 1, carrier gas containing sample components passes through the column 11, in which process the sample components are separated.

The column 11 is housed in a column oven 13 along with a heater, fan, etc. (none of which are illustrated). The column oven 13 has the purpose of heating the column 11, and allows execution of isothermal analysis in which analysis is performed while maintaining a constant temperature inside the column oven 13, temperature-programmed analysis in which analysis is performed while gradually raising the temperature inside the column over 13, and the like.

As the carrier gas, for example, He gas can be used. The carrier gas is supplied via AFC 14 to sample gasification chamber 12. AFC 14 has the purpose of adjusting the flow rate of the carrier gas, and during analysis, the flow rate of carrier gas supplied to the sample gasification chamber 12 is adjusted by AFC 14 so that the carrier gas flows at a constant flow rate through the column 11.

The downstream side of the column 11 branches at splitter unit 16, being connected to FID 15 and MS 2 respectively. An unillustrated APC (Advanced Pressure Controller) is connected to the splitter unit 16, and carrier gas is added to the splitter unit 16. As a result, sample components can be guided to both the FID 15 as the first detector and MS 2 as the second detector to perform analysis.

MS 2 is provided with a vacuum chamber, ion detector and the like (none of which have been illustrated). During analysis, sample components separated by the column 11 are guided into the vacuum chamber which is in a vacuum state. Sample components which have been ionized inside the vacuum chamber can then be detected by the ion detector to perform mass analysis.

The operation of this gas chromatograph/mass spectrometer can be controlled by control unit 3. Control unit 3 has a configuration comprising, for example, a CPU (Central Processing Unit), and is connected to the aforementioned MS 2, AFC 14 and FID 15, as well as to display unit 4 and the like. Display unit 4 comprises, for example, a liquid crystal display. The control unit 3 and display unit 4 constitute a chromatogram display device for displaying chromatograms on the display unit 4. The control unit 3 and display unit 4 can be constituted by means of a personal computer, in which case storage unit 5, described below, may be assigned to a storage unit provided in the personal computer.

In the present embodiment, prior to measurement of a sample which contains or which may contain the target component to be measured (the measurement target sample), a standard solution containing the same target component is measured. It is thereby possible to determine the retention time of the target component contained in the standard sample as the standard retention time. In addition, straight chain alkanes of different carbon count (n-alkanes) are measured as a calibration sample. It is thereby possible to determine, as the calibration retention time, the retention time corresponding to peaks appearing immediately before and after the standard retention time of the target component among the peaks of calibration components appearing in a predetermined time interval. When measuring a measurement target sample, a peak present within a predetermined time range defined with reference to the standard retention time is identified as a peak of the target component.

Figure 2:
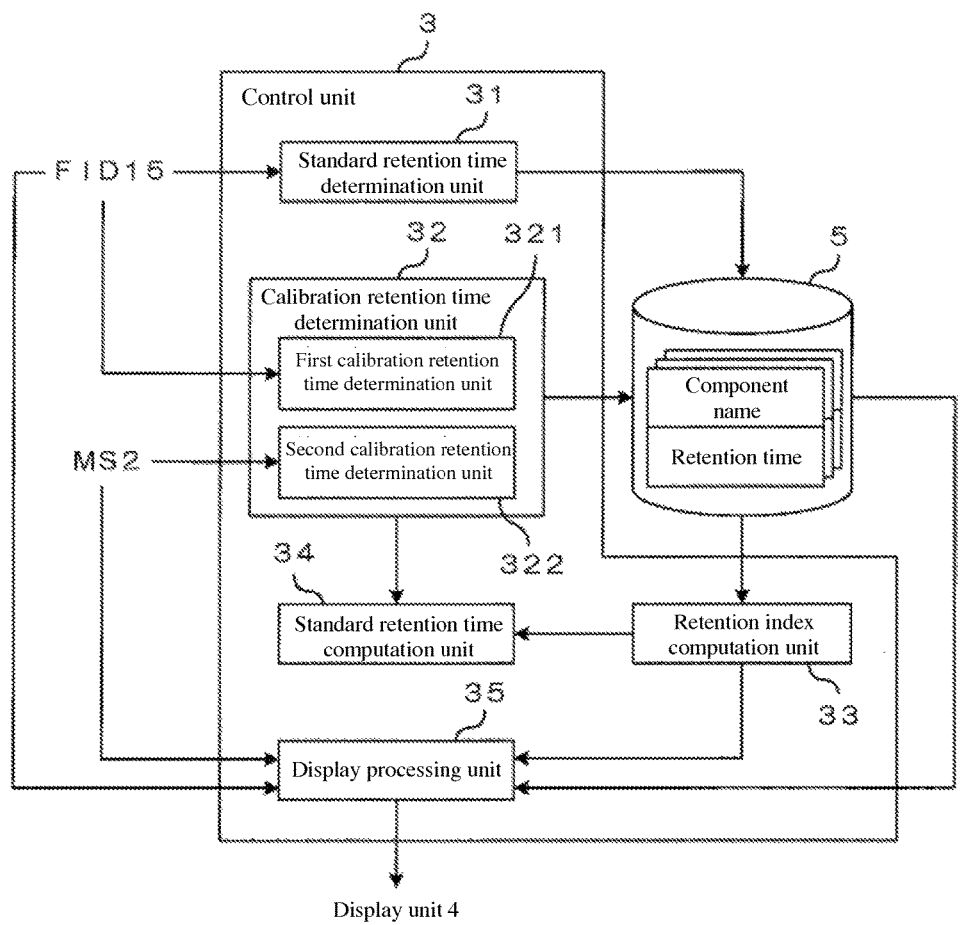
FIG. 2 is a block diagram illustrating an example of the electric configuration in the gas chromatograph/mass spectrometer of FIG. 1.

FIG. 2 is a block diagram illustrating an example of the electrical configuration of the gas chromatograph/mass spectrometer of FIG. 1. Control unit 3 functions as standard retention time determination unit 31, calibration retention time determination unit 32, retention index computation unit 33, standard retention time computation unit 34, display processing unit 35 and the like through execution of a program by the CPU. A storage unit 5 consisting of RAM (Random Access Memory) or the like is connected to the control unit 3.

By performing processing for measuring a standard sample with FID 15, the standard retention time determination unit 31 determines the standard retention time of the target component in FID 15 based on the detection signal from FID 15. The standard retention time of the target component differs not only according to the detector (for example, FID 15 or MS 2) due to differences in distance from the splitter unit 16, but also differs according to various measurement conditions such as the length of the column 11 and the temperature of the column oven 13. The standard retention time of the target component in FID 15 under the measurement conditions present at the time is determined by standard retention time determination unit 31, and that retention time is stored along with the component name in storage unit 5.

Calibration retention time determination unit 32 performs processing for measuring identical calibration samples with FID 15 and MS 2 in order to determine the calibration retention time in FID 15 and MS 2. Calibration retention time determination unit 32 includes a first calibration retention time determination unit 321 and a second calibration retention time determination unit 322. The first calibration retention time determination unit 321 determines the calibration retention time in FID 15 based on the detection signal from FID 15. Furthermore, the second calibration retention time determination unit 322 determines the calibration retention time in MS 2 based on the detection signal from MS 2.

Just as in the case of the standard retention time, the calibration retention time differs not only according to the detector (for example, FID 15 or MS 2) due to differences in distance from the splitter unit 16, but also differs according to various measurement conditions such as the length of the column 11 and the temperature of the column oven 13. The calibration retention time under the measurement conditions present at the time in FID 15 is determined in the first calibration retention time determination unit 321, and that retention time is stored along with the component name in storage unit 5. Furthermore, the calibration retention time under the measurement conditions present at the time in MS 2 is determined in the second calibration retention time determination unit 322, and that retention time is stored along with the component name in storage unit 5.

The retention index computation unit 33 computes the retention index of the target component based on the standard retention time and calibration retention time for the target component in FID 15. The retention index (RI) is represented on the basis of a numerical value obtained by multiplying the carbon count of a straight chain alkane component by 100. For example, if the calibration retention time of a calibration component with a carbon count of 10 in FID 15 ($C_{10}H_{22}$, RI=1000) is 10 minutes, the calibration retention time of a calibration component with a carbon count of 11 ($C_{11}H_{24}$, RI=1100) is 14 minutes, and the standard retention time of the target component contained in the standard sample in FID 15 is 12 minutes, then the retention index of the target component will be determined to be RI=1050.

The standard retention time computation unit 34 computes the standard retention time for the target component based on the calibration retention time and retention index. After the standard retention time has been determined with the standard retention time determination unit 31, if one goes on to measure the measurement target sample using FID 15 under the same measurement conditions, the target component can be identified using that determined standard retention time. However, if one does not go on to measure the measurement target sample using FID 15, even if measurement is later performed with the same FID 15, the standard retention time will change according to the measurement environment at that time, for example, due to change of length of column 11 as a result of maintenance.

Here, rather than measuring both the standard retention time and the calibration retention time again with FID 15, so long as just the calibration retention time is measured, it is possible to compute the standard retention time of the target component in FID 15 based on the calibration retention time in FID 15 determined by the first calibration retention time determination unit 321 and the retention index computed by the retention index computation unit 33. Similarly, so long as just a calibration sample is measured using MS 2, the standard retention time of the target component in MS 2 can be computed based on the calibration retention time in MS 2 determined by the second calibration retention time determination unit 322 and the retention index computed by the retention index computation unit 33.

Assume that, in a case where the retention index of the target component computed by the retention index computation unit 33 is RI=1050, as in the example described above, the calibration retention time of the calibration sample measured subsequently with FID 15 or MS 2 is 9 minutes for a calibration component with a carbon count of 10 ($C_{10}H_{22}$, RI=1000) and 11 minutes for a calibration component with a carbon count of 11 ($C_{11}H_{24}$, RI=1100). In this case, the standard retention time of the target component can be computed to be 10 minutes based on the aforementioned two calibration retention times and the retention index (RI=1050).

The display processing unit 35 displays chromatograms of the measurement target sample measured with FID 15 and MS 2 on display unit 4. Here, the display processing unit 35 displays each chromatogram on the display unit 4 in a time range defined with reference to the retention index computed by the retention index computation unit 33. It should be noted that the chromatogram of the measurement target sample measured in MS 2 is a chromatogram at a certain specified mass (a mass chromatogram).

Figure 3:
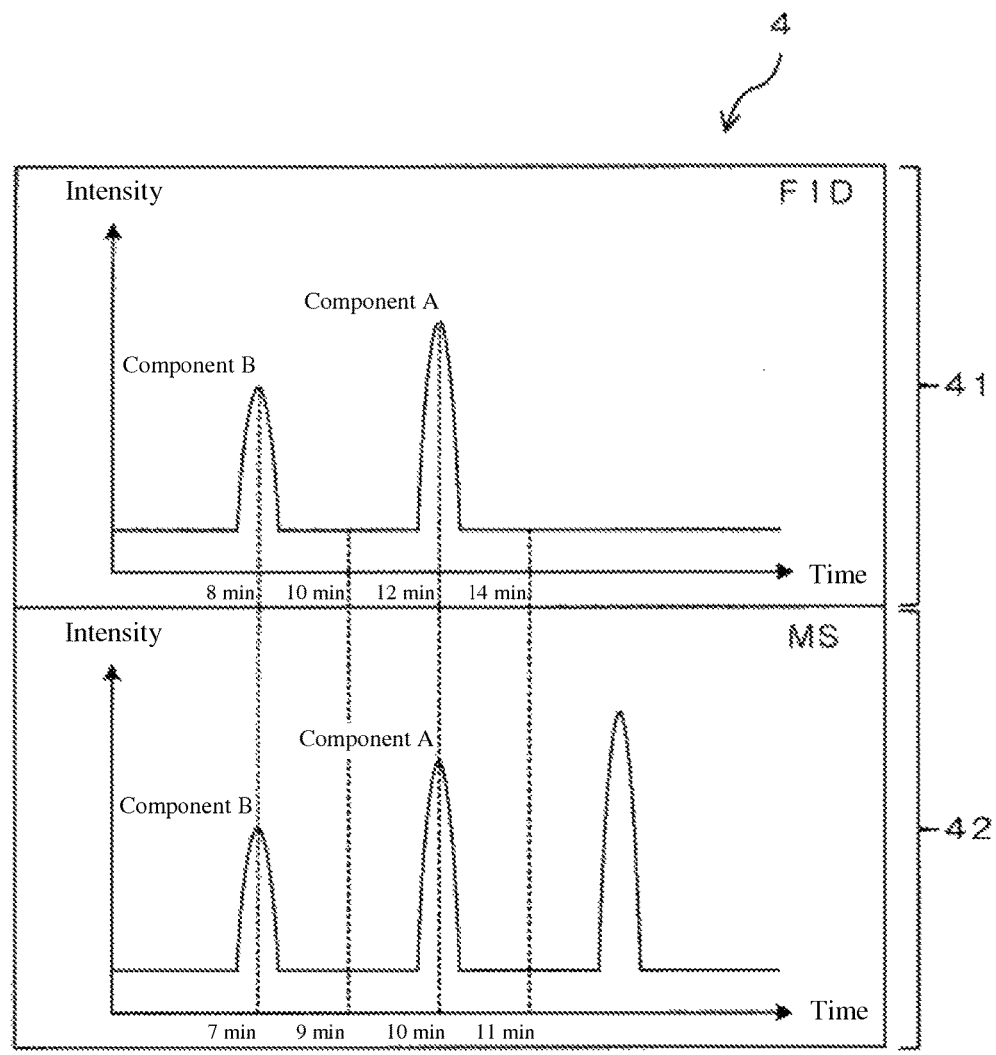
FIG. 3 is a drawing illustrating an example of the chromatograms displayed on the display unit.

FIG. 3 is a drawing illustrating an example of the chromatograms displayed on the display unit 4. In this example, a first display area 41 and a second display area 42 are defined on the display screen of the display unit 4. The chromatogram of the measurement target sample measured with FID 15 is displayed in the first display area 41, and the chromatogram of the measurement target sample measured with MS 2 is displayed in the second display area 42.

Namely, chromatograms of a measurement target sample containing an identical target component (in this example, component A) measured using FID 15 and MS 2 are displayed on the display unit 4. The configuration is however not limited to one where the chromatograms are displayed at once on the display screen of the display unit 4, and a configuration wherein the chromatograms are displayed on the display screen of the display unit 4 in alternation based on user operations is also possible.

In the present embodiment, as described above, chromatograms of the measurement target sample measured with FID 15 and MS 2 are displayed on display unit 4 in a time range defined with reference to the retention index of the target component computed based on the standard retention time and calibration retention time for the target component in FID 15. For example, if the respective chromatograms are displayed in the first display area 41 and second display area 42 in a time range defined with reference to the retention index of component A, which is the target component, the peaks of component A will appear at mutually corresponding positions, as shown in FIG. 3.

Since the retention index is not readily influenced by differences in length of the column 11, by displaying the chromatograms on the display unit 4 in a time range defined with reference to this retention index, the peaks of the target component measured with FID 15 and MS 2 can be displayed in a corresponding time range. Therefore, even in cases where the retention times of the target component in FID 15 and MS 2 differ, the measurement results for an identical target component from FID 15 and MS 2 can be easily compared.

Furthermore, in the present embodiment, the standard retention time of the target component in MS 2 is computed based on the calibration retention time in MS 2 and the retention index of the target component computed based on the standard retention time and calibration retention time for the target component in FID 15. Consequently, there is no need to determine the standard retention time by measuring a standard sample containing the target component using MS 2, and thus the time required for comparing the measurement results for an identical target component from FID 15 and MS 2 can be reduced.

If target component A has been identified by measuring a measurement target sample using FID 15, the component name of that target component A is stored as identification information in storage unit 5 in association with the standard retention time of the target component in FID 15. In the first display area 41 in which the chromatogram of the measurement target sample measured with FID 15 has been displayed, the component name (component A) is displayed at a location corresponding to the standard retention time (for example, 12 minutes) of target component A in FID 15.

Furthermore, in the second display area 42 in which the chromatogram of the measurement target sample measured with MS 2 has displayed, the component name (component A) is displayed at a location corresponding to the standard retention time (for example, 10 minutes) of target component A in MS 2 computed based on the retention index. Namely, the component name of target component A, which has been identified by measuring the measurement target sample with FID 15, is displayed on the chromatogram of the measurement target sample measured with MS 2 based on the retention index. Therefore, the measurement results for the identical target component A from FID 15 and MS 2 can be compared even more easily.

If an unexpected component (in this example, component B) is identified by measuring the measurement target sample with MS 2, the component name of that component B is stored in storage unit 5 as identification information in association with the retention time of that component in MS 2. In the second display area 42 in which the chromatogram for the measurement target sample measured with MS 2 has been displayed, the component name (component B) is displayed at a location corresponding to the retention time (for example, 7 minutes) of this component B in MS 2.

Furthermore, in the first display area 41 in which the chromatogram of the measurement target sample measured with FID 15 has been displayed, the component name (component B) is displayed at a location corresponding to the retention time (for example, 8 minutes) of component B in FID 15 computed based on the retention index. Namely, the component name of component B identified by measuring the measurement target sample using MS 2 is displayed on the chromatogram of the measurement target sample measured using FID 15 based on the retention index. Therefore, the measurement results not just for the target component A but also for the non-target component B can be easily compared.

Figure 4:
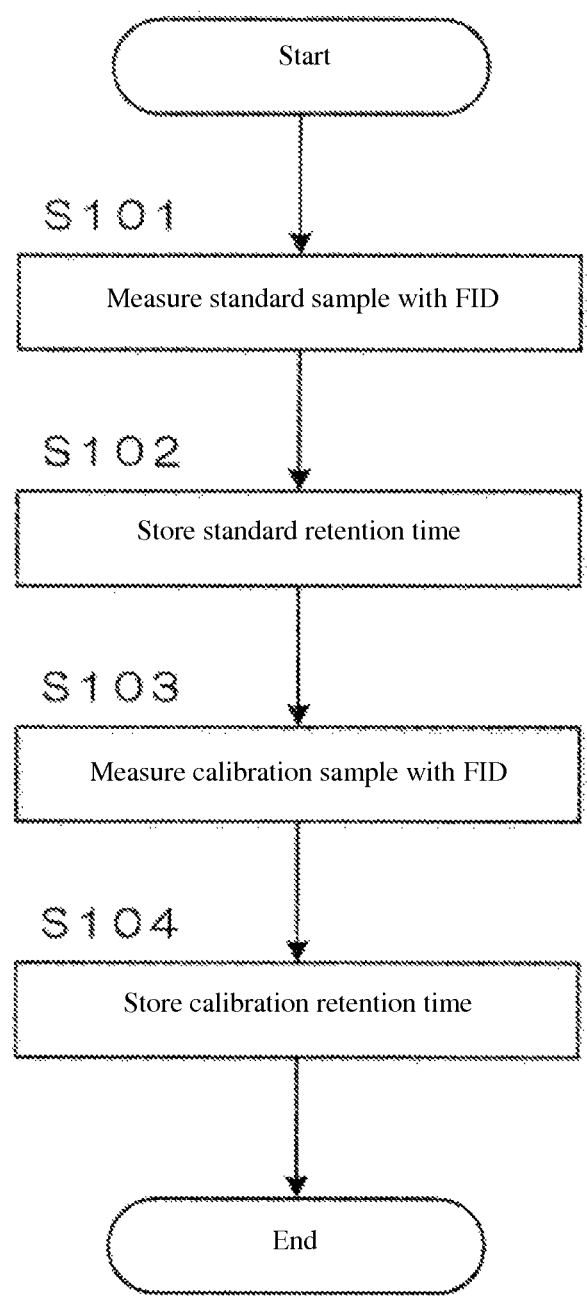
FIG. 4 is a flow chart illustrating an example of the processing performed by the control unit at the preparatory stage prior to computing the retention index of the target component.

FIG. 4 is a flow chart illustrating an example of the processing performed by the control unit 3 at the preparatory stage prior to computing the retention index of the target component. At the preparatory stage, first, the standard retention time of the target component in FID 15 is determined by measuring a standard sample with FID 15 (step S101: standard retention time determination step). The determined standard retention time is stored in storage unit 5 (step S102).

Next, the calibration retention time in FID 15 is determined by measuring a calibration sample with FID 15 (step S103: first calibration retention time determination step). The determined calibration retention time is stored in storage unit 5 (step S104). Through the processing described above, the data necessary for computing the retention index is obtained (the standard retention time and calibration retention time for the target component in FID 15).

Figure 5:
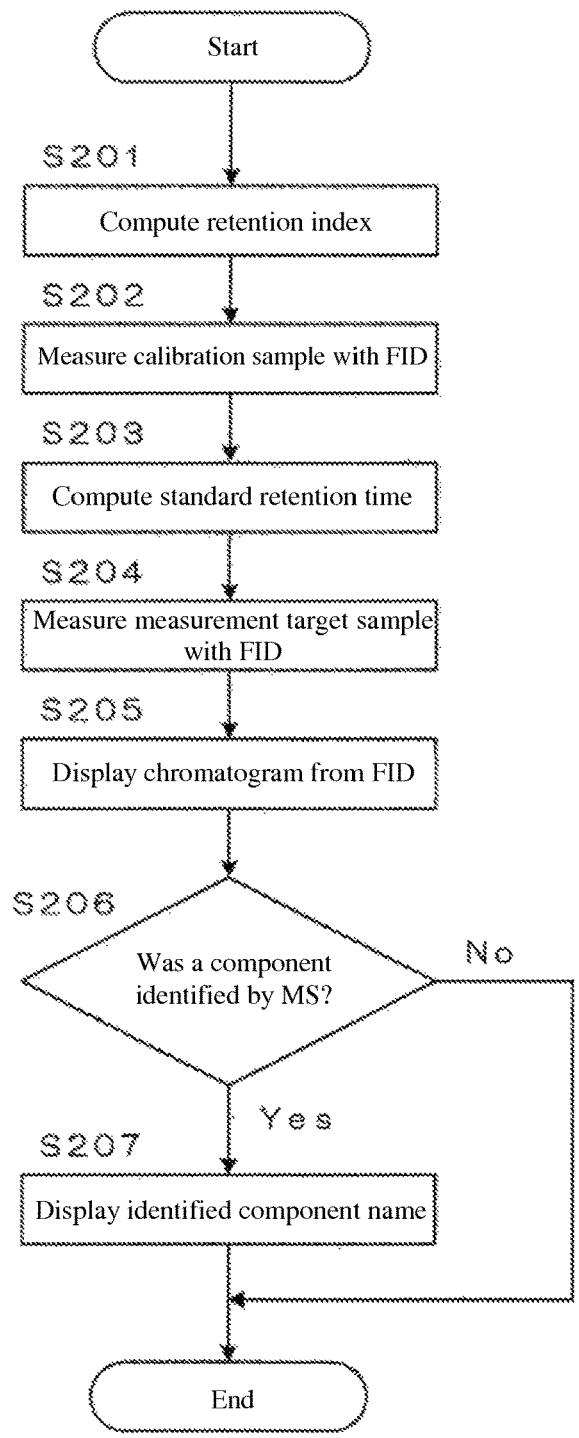
FIG. 5 is a flow chart illustrating an example of the processing performed by the control unit when measuring a measurement target sample with an FID.

FIG. 5 is a flow chart illustrating an example of the processing performed by the control unit 3 when measuring a measurement target sample with FID 15. After the processing shown in FIG. 4, if one goes on to measure the measurement target sample using FID 15 under the same measurement conditions, the target component can be identified using the standard retention time determined in step S101 of FIG. 4. On the other hand, if one does not go on to measure the measurement target sample using FID 15, the retention time may change along with changes in the measurement conditions, such as a change in length of the column 11 due to maintenance, and thus measurement of the measurement target sample is performed with FID 15 according to the processing described below.

To measure the measurement target sample with FID 15, first, the retention index of the target component is computed based on the standard retention time and calibration retention time for the target component in FID 15 stored in storage unit 5 (step S201). The calibration retention time in FID 15 is then determined by measuring a calibration sample with FID 15 (step S202).

Here, by using the retention index, the standard retention time can be computed without measuring the standard sample again. Namely, the standard retention time in FID 15 is computed (step S203) based on the retention index of the target component computed in step S201 and the calibration retention time in FID 15 determined in step S202.

The measurement target sample is then measured with FID 15 (step S204), and the measurement results thereof are displayed as a chromatogram on display unit 4 (step S205: display processing step). Here, as illustrated in FIG. 3, the chromatogram is displayed on display unit 4 (first display area 41) in a time range defined with reference to the retention index. Furthermore, if a component was identified upon measuring a measurement target sample containing the same target component with MS 2 (Yes in step S206), the name of that identified component is displayed on the chromatogram based on the retention index (step S207).

Figure 6:
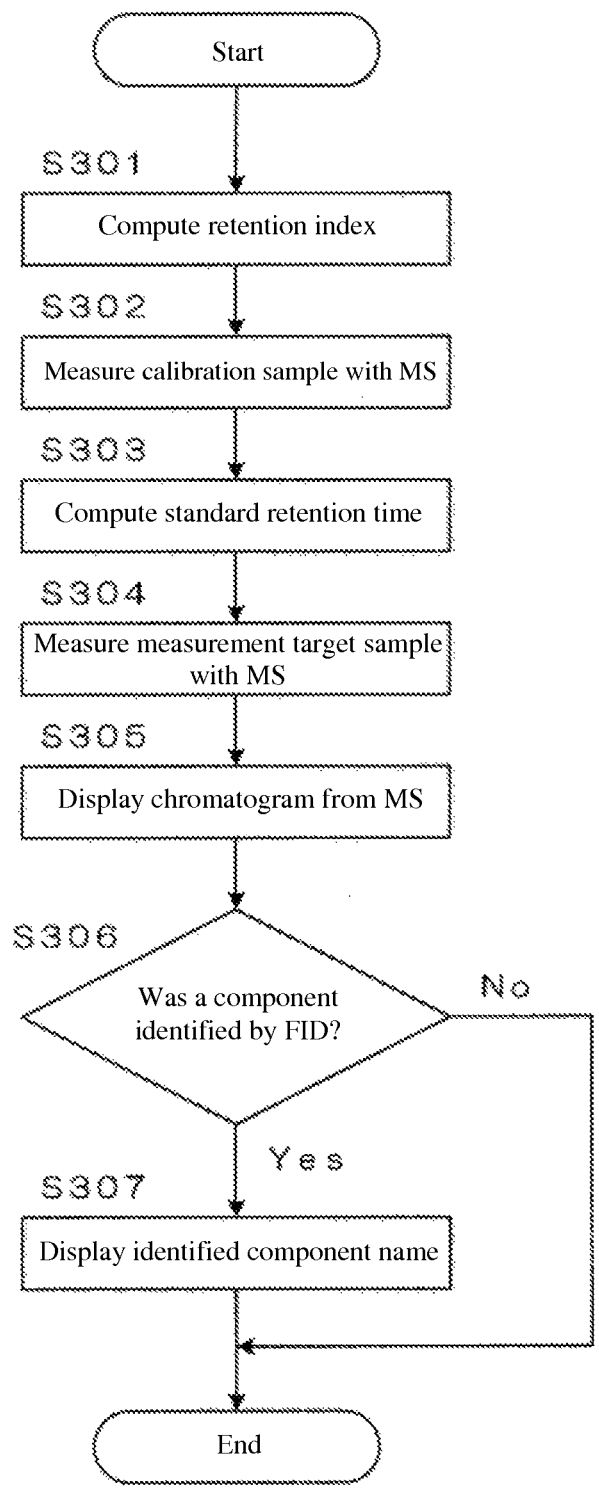
FIG. 6 is a flow chart illustrating an example of the processing performed by the control unit when measuring a measurement target sample with an MS.

FIG. 6 is a flow chart illustrating an example of the processing performed by the control unit 3 when measuring a measurement target sample with MS 2. To measure the measurement target sample with MS 2, first, the retention index of the target component is computed based on the standard retention time and calibration retention time for the target component in FID 15 stored in storage unit 5 (step S301: retention index computation step). The calibration retention time in MS 2 is then determined by measuring a calibration sample with MS 2 (step S302: second calibration retention time determination step).

Here, by using the retention index, the standard retention time can be computed without measuring the standard sample again. Namely, the standard retention time in MS 2 is computed (step S303: standard retention time computation step) based on the retention index of the target component computed in step S301 and the calibration retention time in MS 2 determined in step S302.

The measurement target sample is then measured with MS 2 (step S304), and the measurement results thereof are displayed as a chromatogram on display unit 4 (step S305: display processing step). Here, as illustrated in FIG. 3, the chromatogram is displayed on display unit 4 (second display area 42) in a time range defined with reference to the retention index. Furthermore, if a component was identified upon measuring a measurement target sample containing the same target component with FID 15 (Yes in step S306), the name of that identified component is displayed on the chromatogram based on the retention index (step S307).

In the above embodiment, a configuration was described wherein identified component names (for example, component A, component B, etc.) are displayed automatically on the chromatograms. However, the configuration is not limited thereto, and for example, a configuration whereby the component name of a selected component is displayed on the chromatogram based on user operations is also possible. Furthermore, the identification information of components displayed on a chromatogram need only be information that allows identification of the component and is not limited to component names, and can be, for example, a chemical formula or other symbols.

The configuration is not limited to one wherein the retention time in FID 15 and the retention time in MS 2 are stored in a single storage unit 5, and a configuration wherein these are stored in separate storage units 5 is also possible.

Furthermore, in the above embodiment, a case was described where the first detector was FID 15 and the second detector was MS 2, but the invention is not limited to such a configuration. Here, various other detectors, such as ECD, FPD, etc. can also be used as the first detector and second detector.

Furthermore, in the above embodiment, a case was described wherein chromatograms of a measurement target sample measured in a first detector (FID 15) and second detector (MS 2) provided in a single chromatograph/mass spectrometer device were displayed on display unit 4, but the present invention can also be applied in cases where the measurement results from a first detector and second detector provided in different devices are to be compared.

Chromatographs to which the present invention can be applied are not limited to gas chromatograph/mass spectrometers and can also be gas chromatographs not comprising MS 2, as well as liquid chromatographs. Furthermore, the chromatogram display device may be provided separately from the chromatograph. In this case, chromatograms can be displayed by the chromatogram display device to which the present invention has been applied without modification to the configuration of the chromatograph.

EXPLANATION OF REFERENCES

1 GC
2 MS
3 Control unit
4 Display unit
5 Storage unit
11 Column
12 Sample gasification chamber
13 Column oven
14 AFC
15 FID
16 Splitter unit
31 Standard retention time determination unit
32 Calibration retention time determination unit
33 Retention index computation unit
34 Standard retention time computation unit
35 Display processing unit
41 First display area
42 Second display area
321 First calibration retention time determination unit
322 Second calibration retention time determination unit

What is claimed:

1. A chromatogram display method for displaying, on a display unit, chromatograms of a measurement target sample containing an identical target component measured using a first detector and a second detector, said chromatogram display method comprising:
    generating a standard retention time of the target component in said first detector by measuring a standard sample containing the target component with said first detector;
    generating a calibration retention time in said first detector by measuring a calibration sample containing a calibration component with said first detector;
    generating a retention index for the target component based on the standard retention time and the calibration retention time for the target component in said first detector;
    generating a calibration retention time in said second detector by measuring said calibration sample with said second detector;
    generating a standard retention time of the target component in the second detector based on the calibration retention time in said second detector and said retention index; and
    display processing, wherein in said display processing, chromatograms of the measurement target sample measured with said first detector and said second detector are displayed with the standard retention times of the target component in said first detector and said second detector on said display unit in a corresponding time range defined with reference to said retention index, wherein a time axis of at least one of the chromatograms has unequal intervals of time.

2. The chromatogram display method as described in claim 1, wherein, in said display processing, identification information for the target component identified by measuring the measurement target sample with said first detector is displayed, on the chromatogram of the measurement target sample measured with said second detector, based on said retention index.

3. The chromatogram display method as described in claim 2, wherein, in said display processing, identification information for components other than the target component identified by measuring the measurement target sample with said second detector is displayed, on the chromatogram of the measurement target sample measured with said first detector, based on said retention index.

4. The chromatogram display method as described in claim 1, wherein, in said display processing, identification information for components other than the target component identified by measuring the measurement target sample with said second detector is displayed, on the chromatogram of the measurement target sample measured with said first detector, based on said retention index.

5. The chromatogram display method as described in claim 1, wherein, in said display processing step, chromatograms of the measurement target sample, measured with said first detector and said second detector, are displayed simultaneously on said display unit in a mutually corresponding time range defined with reference to said retention index.

6. The chromatogram display method as described in claim 1, wherein, in said display processing step, the peaks of the target component measured with said first detector and said second detector are displayed on said display unit in a mutually corresponding time range defined with reference to said retention index.

7. The chromatogram display method as described in claim 1, wherein, in said display processing step, the peaks of the target component, measured with said first detector and said second detector, are displayed simultaneously on said display unit in a mutually corresponding time range defined with reference to said retention index.

8. The chromatogram display method as described in claim 1, wherein the first detector is one of a Mass Spectrometer (MS) or a Flame Ionization Detector (FID), and the second detector is the other one of the Mass Spectrometer (MS) or the Flame Ionization Detector (FID).

9. The chromatogram display device as described in claim 1, wherein said display unit displays times for the chromatograms of the measurement target sample measured with said first detector and said second detector.

10. A chromatogram display device for displaying, on a display unit, chromatograms of a measurement target sample containing an identical target component measured using a first detector and a second detector, said chromatogram display device comprising:
    a standard retention time determination unit which generates the standard retention time of the target component in said first detector by measuring a standard sample containing the target component with said first detector;
    a first calibration retention time determination unit which generates the calibration retention time in said first detector by measuring a calibration sample containing a calibration component with said first detector;
    a retention index computation unit which generates a retention index for the target component based on the standard retention time and the calibration retention time for the target component in said first detector;

a second calibration retention time determination unit which generates the calibration retention time in said second detector by measuring said calibration sample with said second detector;

a standard retention time computation unit which generates the standard retention time of the target component in the second detector based on the calibration retention time in said second detector and said retention index; and a display processing unit which displays chromatograms of the measurement target sample measured with said first detector and said second detector on said display unit with the standard retention times of the target component in said first detector and said second detector in a corresponding time range defined with reference to said retention index, wherein a time axis of at least one of the chromatograms has unequal intervals of time.

11. The chromatogram display device as described in claim 10, wherein said display processing unit displays identification information for the target component identified by measuring the measurement target sample with said first detector, on the chromatogram of the measurement target sample measured with said second detector, based on said retention index.

12. The chromatogram display device as described in claim 11, wherein said display processing unit displays identification information for components other than the target component identified by measuring the measurement target sample with said second detector, on the chromatogram of the measurement target sample measured with said first detector, based on said retention index.

13. The chromatogram display device as described in claim 10, wherein said display processing unit displays identification information for components other than the target component identified by measuring the measurement target sample with said second detector, on the chromatogram of the measurement target sample measured with said first detector, based on said retention index.

14. A chromatograph, comprising:
the chromatogram display device as described in claim 10;
the first detector; and
the second detector.

15. The chromatogram display device as described in claim 10, wherein said display processing unit displays chromatograms of the measurement target sample, measured with said first detector and said second detector, simultaneously on said display unit in a mutually corresponding time range defined with reference to said retention index.

16. The chromatogram display device as described in claim 10, wherein said display processing unit displays the peaks of the target component, measured with said first detector and said second detector, on said display unit in a mutually corresponding time range defined with reference to said retention index.

17. The chromatogram display device as described in claim 10, wherein said display processing unit displays the peaks of the target component, measured with said first detector and said second detector, simultaneously on said display unit in a mutually corresponding time range defined with reference to said retention index.

18. A chromatograph comprising:
the chromatogram display device as described in claim 10, the first detector, and
the second detector, wherein
the first detector is one of a Mass Spectrometer (MS) or a Flame Ionization Detector (FID), and the second detector is the other one of the Mass Spectrometer (MS) or the Flame Ionization Detector (FID).

19. The chromatogram display device as described in claim 10, wherein said display processing unit displays times for the chromatograms of the measurement target sample measured with said first detector and said second detector.

* * * * *